US012414792B2

(12) United States Patent
Turano et al.

(10) Patent No.: US 12,414,792 B2
(45) Date of Patent: Sep. 16, 2025

(54) MICRODEBRIDER WITH STABILITY INTERFACE BUSHING

(71) Applicant: Medtronic Xomed, LLC, Jacksonville, FL (US)

(72) Inventors: Bo D. Turano, Jacksonville, FL (US); Erik Papenfuss, Naples, FL (US)

(73) Assignee: Medtronic Xomed LLC, Minneapolis, MN (US)

( * ) Notice: Subject to any disclaimer, the term of this patent is extended or adjusted under 35 U.S.C. 154(b) by 341 days.

(21) Appl. No.: 17/900,349

(22) Filed: Aug. 31, 2022

(65) Prior Publication Data

US 2024/0065718 A1 Feb. 29, 2024

(51) Int. Cl.
*A61B 17/32* (2006.01)
*A61B 17/00* (2006.01)

(52) U.S. Cl.
CPC .......... *A61B 17/32002* (2013.01); *A61B 2017/00367* (2013.01); *A61B 2017/00526* (2013.01); *A61B 2217/005* (2013.01)

(58) Field of Classification Search
CPC .............. A61B 17/24; A61B 17/32002; A61B 17/320783
See application file for complete search history.

(56) References Cited

U.S. PATENT DOCUMENTS

| | | | |
|---|---|---|---|
| 4,958,932 A * | 9/1990 | Kegelman | A61B 5/1076 600/172 |
| 5,618,293 A | 4/1997 | Sample et al. | |
| 6,007,556 A | 12/1999 | Kablik et al. | |
| 6,645,218 B1 | 11/2003 | Cassidy et al. | |
| 6,824,552 B2 | 11/2004 | Robison et al. | |
| 7,077,845 B2 | 7/2006 | Hacker et al. | |
| 7,244,263 B2 | 7/2007 | Robison et al. | |
| 7,674,263 B2 | 3/2010 | Ryan | |
| 7,699,846 B2 | 4/2010 | Ryan | |
| 7,719,437 B2 | 5/2010 | Bertram, III | |
| 7,803,170 B2 | 9/2010 | Mitusina | |
| 7,854,736 B2 | 12/2010 | Ryan | |
| 7,942,880 B2 | 5/2011 | Bertram, III | |
| 7,993,360 B2 | 8/2011 | Hacker et al. | |

(Continued)

OTHER PUBLICATIONS

Extended European Search Report EP23193270.8 dated Jan. 15, 2024, 6pp.

*Primary Examiner* — Erin McGrath

(74) *Attorney, Agent, or Firm* — Carter, DeLuca & Farrell LLP

(57) ABSTRACT

A device for removing tissue or bone includes a housing having an outer tube defining an inner lip. A middle tube is supported within the outer tube and includes an opening having teeth at a distal end thereof and a shoulder defined around an outer surface thereof proximate the opening. An inner tube is disposed within the middle tube and includes an opening having teeth at a distal end thereof in registration with the opening in the middle tube. The inner tube couples to a power source and rotates relative to the middle tube such that the teeth cooperate to cut tissue or bone disposed in a cutting window between the openings. A bushing is disposed atop the middle tube against the shoulder, such that, upon assembly, the bushing seats between the shoulder of the middle tube and the inner lip of the outer tube to provide stability therebetween.

11 Claims, 5 Drawing Sheets

(56) References Cited

U.S. PATENT DOCUMENTS

| | | |
|---|---|---|
| 8,052,706 B2 | 11/2011 | Mitusina |
| 8,057,500 B2 | 11/2011 | Mitusina |
| 8,142,464 B2 | 3/2012 | Mitusina |
| 8,366,559 B2 | 2/2013 | Papenfuss et al. |
| 8,808,375 B2 | 8/2014 | Bertram, III |
| 8,852,191 B2 | 10/2014 | Bertram, III |
| 8,870,893 B2 | 10/2014 | Makower et al. |
| 8,944,926 B2 | 2/2015 | Kramer et al. |
| 9,198,685 B2 | 12/2015 | Edwards et al. |
| 9,381,032 B2 | 7/2016 | Edwards et al. |
| 9,474,541 B2 | 10/2016 | Zider et al. |
| 9,486,232 B2 | 11/2016 | Heisler et al. |
| 9,517,076 B2 | 12/2016 | Papenfuss |
| 9,603,607 B2 | 3/2017 | Papenfuss |
| 9,668,751 B2 | 6/2017 | Papenfuss |
| 9,775,967 B2 | 10/2017 | Hatta et al. |
| 9,808,867 B2 | 11/2017 | Krause et al. |
| 9,833,249 B2 | 12/2017 | Bertram, III |
| 9,839,441 B2 | 12/2017 | Hayes et al. |
| 10,179,002 B2 | 1/2019 | Wasicek et al. |
| 10,271,830 B2 | 4/2019 | Papenfuss et al. |
| 10,492,800 B2 | 12/2019 | Papenfuss |
| 10,524,820 B2 | 1/2020 | Algawi et al. |
| 10,743,912 B2 | 8/2020 | Papenfuss |
| 10,779,806 B2 | 9/2020 | Kieturakis et al. |
| 11,020,139 B2 | 6/2021 | Curtin et al. |
| 11,064,980 B2 | 7/2021 | Papenfuss et al. |
| 11,065,012 B2 | 7/2021 | Edwards |
| 2005/0277970 A1* | 12/2005 | Norman .......... A61B 17/32002 606/180 |
| 2019/0357924 A1 | 11/2019 | Papenfuss |
| 2020/0245854 A1* | 8/2020 | Mach ................ A61B 1/00167 |
| 2021/0282799 A1* | 9/2021 | Curtin ............. A61B 17/32002 |
| 2022/0015821 A1 | 1/2022 | Norton et al. |
| 2022/0133360 A1 | 5/2022 | Papenfuss et al. |

\* cited by examiner

MICRODEBRIDER WITH STABILITY INTERFACE BUSHING

FIELD

The present disclosure is generally directed to devices and systems for cutting and treating tissue, such as bone and soft tissue. The present disclosure may be particularly suitable for sinus applications and nasopharyngeal/laryngeal procedures.

BACKGROUND

Devices and systems in accordance with the present disclosure may be suitable for a variety of procedures including ear, nose and throat (ENT) procedures, head and neck procedures, otology procedures, including otoneurologic procedures. Other surgical procedures suitable for use with the devices described herein include: mastoidectomies; nasopharyngeal and laryngeal procedures such as tonsillectomies, tracheal procedures, adenoidectomies, laryngeal lesion removal, and polypectomies; for sinus procedures such as polypectomies, septoplasties, removals of septal spurs, antrostomies, frontal sinus trephination and irrigation, sinus opening, endoscopic DCR, correction of deviated septum s and trans-sphenoidal procedures; rhinoplasty and removal of fatty tissue in the maxillary and mandibular regions of the face.

Of particular significance is the usefulness of the devices and systems described herein with sinus surgery which is often challenging due to the obvious location of the sinus cavity to sensitive organs such as the eyes and brain. Moreover, the relatively small size of the anatomy of interest to the surgeon and the complexity of the typical procedures places a heavy emphasis on precision. Examples of deriders with mechanical cutting components are described in commonly-owned U.S. Pat. Nos. 5,685,838; 5,957,881; and 6,293,957, the entire contents of each of which being incorporated by reference herein.

The Medtronic Straightshot® Microdebriders, e.g., Medtronic Straightshot® RAD40 or RAD60 Microdebriders, use sharp cutters to cut tissue, and suction to withdraw tissue. While tissue debridement with the Medtronic microdebrider systems is a simple and safe technique, the blade angle of the middle tube and the concentric inner rotating tube of these devices relative to the outer tube may vary from about 12 degrees to about 120 degrees. Depending on the angle, the middle tube and the inner tube may extend several centimeters from the distal end of the outer tube, which in some instance can promote instability especially when the inner tube is rotating at high rpms and encountering heavy tissue or bone. Moreover, since one of the unique advantages of the Medtronic Straightshot® Microdebriders is the ability to rotate the cooperating inner and middle cutting tubes 360 degrees to excise tissue and bone without rotating the outer tube, the forces associated with cutting tissue or bone in one rotational position may place more stress on the middle tube and outer tube interface than a different rotational position. As such, a need exists to provide a stabilizing interface between the middle and outer tubes for all blade angles that works during all cutting rotational positions.

SUMMARY

Provided in accordance with the present disclosure is a device for removing tissue or bone including a housing having an outer tube extending therefrom having a longitudinal axis defined therealong, the outer tube including a distal end defining an inner lip. A middle tube is operably supported concentrically within the outer tube, the middle tube including an opening having a series of teeth at a distal end thereof and a shoulder defined around an outer peripheral surface thereof.

An inner tube is concentrically disposed within the middle tube and includes an opening having a series of teeth at a distal end thereof in longitudinal registration with the opening in the middle tube. The inner tube is adapted to couple to a power source such that, upon activation thereof, the inner tube rotates relative to the middle tube and the series of teeth of the inner tube cooperate with the series of teeth of middle tube to cut tissue or bone disposed in a cutting window between the openings defined therebetween. A bushing is disposed atop the middle tube in abutting relation against the shoulder, such that, upon assembly, the bushing seats between the shoulder of the middle tube and the inner lip of the outer tube.

In aspects according to the present disclosure, the distal end is rolled and reamed to form the inner lip.

In aspects according to the present disclosure, the inner tube defines a lumen therethrough and extending therealong from the opening, and a portion of the lumen is adapted to connect to a suction source for eliminating cut tissue or bone.

In aspects according to the present disclosure, a channel is defined between the concentric inner and middle tubes along a length thereof for passing a fluid therealong from a fluid source.

In aspects according to the present disclosure, the device further includes a rotating wheel disposed atop the housing. The rotating wheel is configured to permit selective orientation of the cutting window between respective openings between the middle and inner tubes 360° of rotation without repositioning the outer tube.

Provided in accordance with the present disclosure is a system for removing tissue or bone, the system including a housing adapted to be connected to a power source, a fluid source and a suction source. The housing includes an adapter configured to operably connect to a selectively removable blade. The selectively removable blade has a blade angle of about 12° to about 90°, with the blade including: an outer tube extending therefrom including a longitudinal axis defined therealong, the outer tube including a distal end defining an inner; a middle tube operably supported concentrically within the outer tube, the middle tube including an opening having a series of teeth at a distal end thereof and a shoulder defined around an outer peripheral surface thereof; an inner tube concentrically disposed within the middle tube including an opening having a series of teeth at a distal end thereof in longitudinal registration with the opening in the middle tube, the inner tube adapted to couple to a power source such that, upon activation thereof, the inner tube rotates relative to the middle tube and the series of teeth of the inner tube cooperate with the series of teeth of middle tube to cut tissue or bone disposed in a cutting window defined in the openings defined therebetween; and a bushing disposed atop the middle tube in abutting relation against the shoulder, such that, upon assembly, the bushing seats between the shoulder of the middle tube and the inner lip of the outer tube.

In aspects according to the present disclosure, the system is configured to cooperate with a surgical navigation system.

In aspects according to the present disclosure, the distal end of the outer tube is rolled and reamed to form the inner lip.

In aspects according to the present disclosure, the inner tube defines a lumen therethrough and extending therealong from the opening, a portion of the lumen adapted to connect to the suction source for eliminating cut tissue or bone.

In aspects according to the present disclosure, a channel is defined between the concentric inner and middle tubes along a length thereof for passing a fluid therealong from the fluid source.

In aspects according to the present disclosure, the housing further includes a rotating wheel disposed thereon, the rotating wheel configured to permit selective orientation of the cutting window between respective openings between the middle and inner tubes 360° of rotation without repositioning the outer tube.

BRIEF DESCRIPTION OF THE DRAWINGS

In the drawings, where like numerals refer to like components throughout several views.

DETAILED DESCRIPTION

Figure 1:
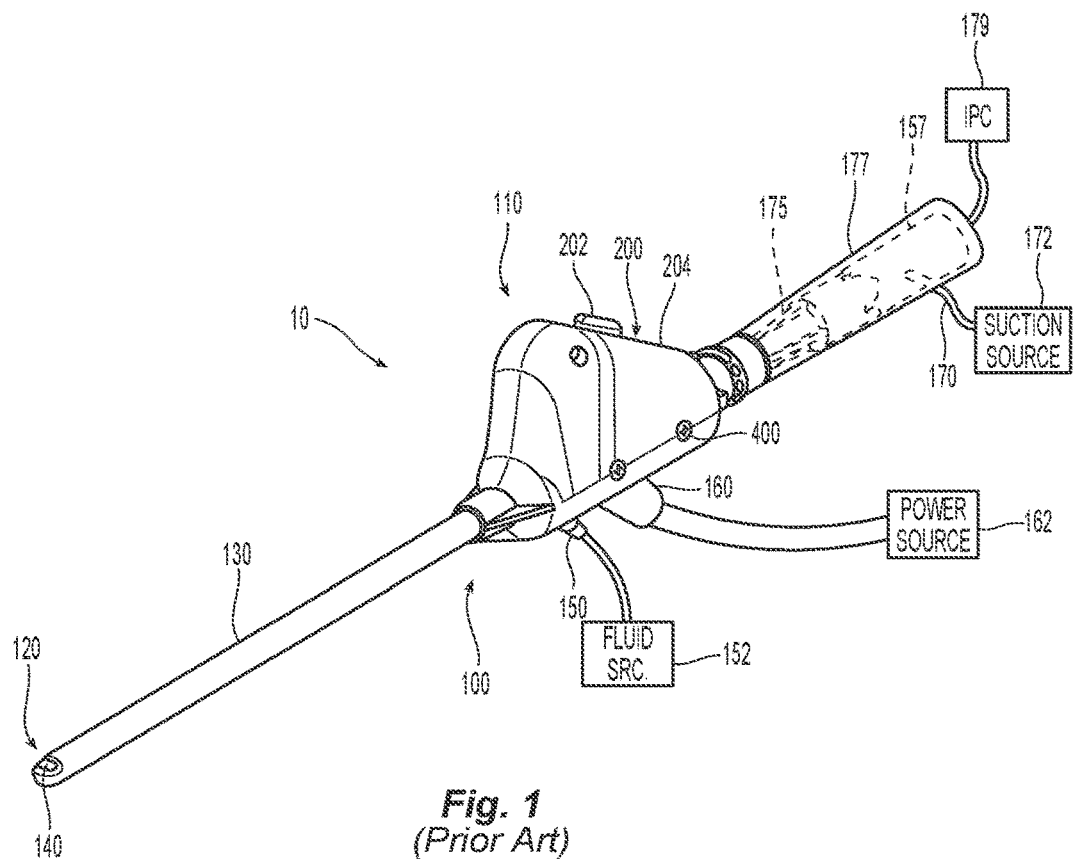
FIG. 1 is a perspective view of a prior art system for performing one or more ENT surgical procedures.

FIG. 1 illustrates a prior art system 10 having a surgical device 100 including a distal end region indicated generally at 120 and a proximal end region indicated generally at 110. The device 100 includes an outer shaft 130 and an inner shaft 140 coaxially maintained within the outer shaft 130. A portion of the inner shaft 140 is shown in FIG. 1 at distal end region 120. Proximal end region 110 includes a button activation cell 200 having a housing 204 and an activation button 202, the proximal end region further including a hub 175 coupled to inner shaft 140. The hub 175 is configured to operably couple to a handpiece 177, which can be manipulated by a user (e.g., a surgeon). The handpiece 177, in turn, may be coupled to an integrated power console or IPC 179 for driving the device 100 and, specifically, for controlling rotation of inner shaft 140. The IPC 179 may also include a fluid source (not shown) for providing fluid to device 100.

Proximal end region 110 also includes a fluid source connector 150, a power source connector 160 and a suction source connector 170 operably connected to a fluid source 152, a power source 162, and a suction source 172, respectively, of system 10. While saline is particularly useful with the present disclosure, other fluids are contemplated. Power source 162, e.g., a generator, is an optional component of system 10 and may be designed for use with bipolar energy. For example, the Transcollation® sealing energy supplied by the Aquamantys® System may be used. Both the fluid source 152 and suction source 172 are also optional components of system 10. However, use of fluid in conjunction with energy delivery may provide additional tissue benefits.

In use, a fluid (e.g., saline) may be emitted from an opening at the distal end region of the device 100. Tissue fragments and fluids can be removed from a surgical site through an opening (not shown in FIG. 1) in the distal end region via the suction source 172, as will be further explained below.

Figure 2:
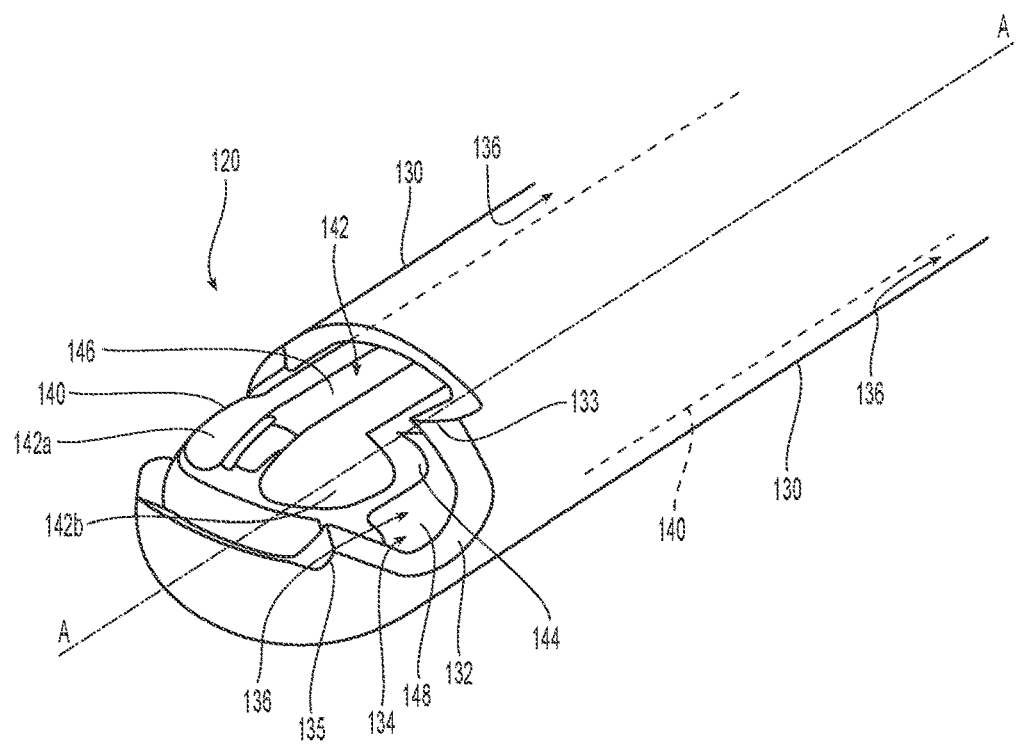
FIG. 2 is an enlarged, perspective view of a distal end of a blade for use with the system of FIG. 1.

FIG. 2 shows an enlarged perspective view of distal end portion 120 of device 100. It is important to note that shaft 130 may be selectively engaged with housing 204 such that various cutters 132 at various angles may be utilized for various surgical purposes, e.g., FIGS. 6-8 discussing the Medtronic Straightshot® M4 or M5.

Figure 3:
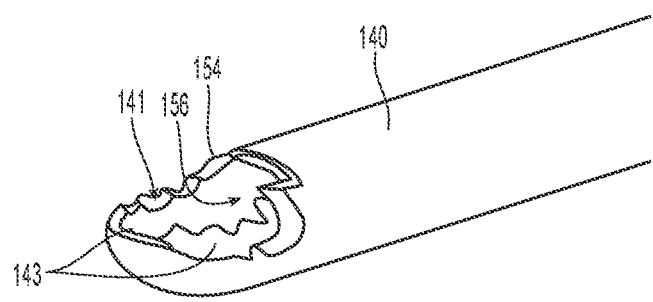
FIG. 3 is an enlarged, perspective view of a distal end of another blade for use with the system of FIG. 1.

The outer shaft 130 includes an opening 134 at a distal end 135 of the outer shaft 130. Opening 134 is defined by cutters 132, which includes cutting teeth 133. The outer shaft 130 may be rigid or malleable (or combinations thereof) and may be made of a variety of metals and/or polymers or combinations thereof, e.g., stainless steel. A distal portion 148 of inner shaft 140 can be seen through the opening 134 of outer shaft 130. In FIG. 1, inner shaft 140 is depicted in a position such that an inner shaft cutter 141 (FIG. 3), including cutting teeth 143, is facing an inner wall (not shown) of outer shaft 130. Cutter 141 defines an inner shaft opening 154 (FIG. 3). Outer and inner shaft cutters 132 and 141 may move relative to one another in oscillation or rotation (or both) in order to mechanically cut tissue. For example, outer shaft cutter 132 may remain stationary relative to the hub 175 while the inner shaft cutter 141 may rotate about a longitudinal axis A-A defined through the device 100 (FIG. 2), thereby cutting tissue.

Rotation of inner shaft 140 may be achieved via manipulation of hub 175 (FIG. 1) that can orient the inner shaft 140 relative to the outer shaft 130 and may additionally allow for locking of the inner shaft 140 relative to the outer shaft 130 in a desired position, i.e., inner shaft 140 may be locked in position when cutter 141 is facing down and an electrode assembly 142 is facing up. As described above, hub 175 may be connected to handpiece 177, which may be controlled by an ITC 179. Alternatively, the hub 175 and/or handpiece 177 may be manipulated manually.

Inner shaft 140 may be selectively rotated to expose electrode assembly 142 including electrodes 142a, 142b, through opening 134 of outer shaft 130, as shown in FIG. 2. As depicted in FIG. 2, inner shaft 140 is positioned such that the inner shaft cutter 141 is facing the interior (not shown) of outer shaft 130 and may be in a downward facing direction and include a downward position. In the downward position, tissue is shielded from the inner shaft cutter 141 during hemostasis (via energy delivery through electrodes 142a, 142b), thereby delivering energy to tissue with no attendant risk that the cutting teeth 143 of the inner shaft 140 will diminish the efforts to achieve hemostasis. Device 100 may thus include two modes: a cutting or debridement mode and a sealing or hemostasis mode and the two modes may be mutually exclusive, i.e., hemostasis is achieved via energy delivery to tissue while cutters 132, 141 are not active or cutting. As described below, energy may be advantageously delivered simultaneously with a fluid such as saline to achieve an optimal tissue effect by delivering controlled RF energy to tissue.

As depicted in FIG. 3, when the inner shaft 140 is oriented such that cutter 141 is in the downward position, rotating inner shaft 140 approximately 180 degrees relative to the outer shaft 130 will expose inner shaft cutter 141 and inner shaft opening 154 through the outer shaft opening 134.

When the inner shaft cutter 141 is positioned as shown in FIG. 3, the inner shaft cutter 141 may be in an upward position. The inner shaft opening 154 is fluidly connected to an inner shaft lumen 156 that extends from the inner shaft distal portion 148 to the proximal end 151 of inner shaft 140 and may be fluidly connected with the suction source 172. With this configuration, tissue cut via inner and outer shaft cutters 141, 132 may be aspirated into the inner shaft lumen 156 through the inner shaft opening 154 upon application of suction source 172, thereby removing tissue from a target site.

Figure 4:
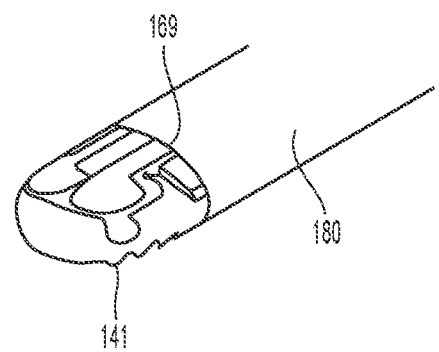
FIGS. 4 and 5 are enlarged, perspective views of distal ends of a blade for use with the system of FIG. 1.
Figure 5:
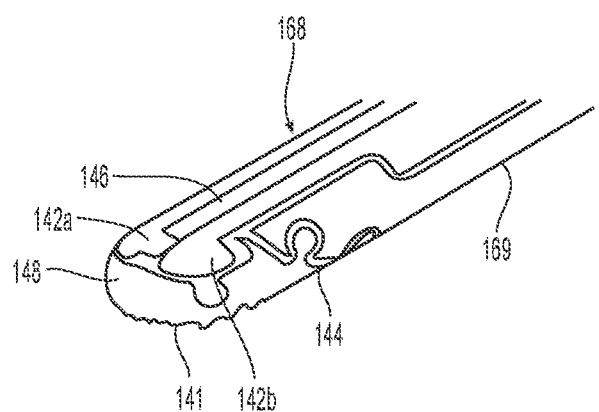

With reference between FIGS. 4 and 5, the inner shaft 140 includes a proximal assembly 168 including a proximal assembly shaft component 169 (more clearly seen in FIG. 5) and electrodes 142a and 142b. Electrodes 142a and 142b may be used to deliver any suitable energy for purposes of coagulation, hemostasis or sealing of tissue. Electrodes 142a and 142b are particularly useful with fluid, such as saline, provided by fluid source 152 (FIG. 1) which may be emitted near the outer shaft opening 134. Outer shaft opening 134 is fluidly connected to an outer shaft lumen 136 that extends from outer shaft opening 134 to the proximal end region 110 of device 100 and may be fluidly connected to the fluid source 152 (FIG. 1). Thus, fluid can be delivered to the opening 134 of outer shaft. 130 and interacts with electrode 142a, 142b.

Figure 6:
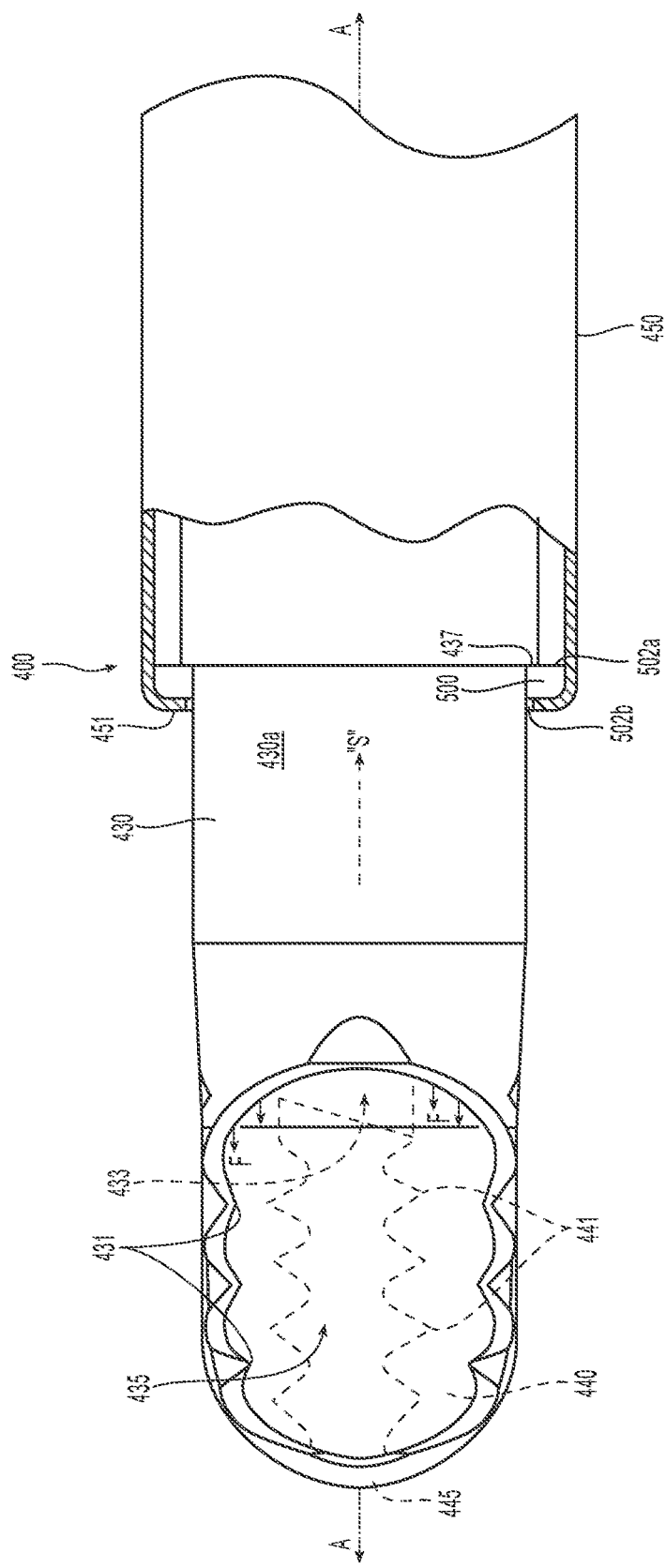
FIG. 6 is an enlarged, top view of a distal end of a blade in accordance with the present disclosure.

Turning to FIG. 6, which shows a schematic cross-section of a surgical blade 400 (which is selectively engageable with a portion of device 100 above, e.g., housing 204) of the present disclosure for use with the surgical system 10 described above and in connection with various ENT procedures, such as transnasal endoscopic bone and tissue removal under navigation or under navigation with devices that utilize irrigation and suction to help maximize visibility during surgery. Similar to the above-described components of device 100, blade 400 is configured to connect to the one or more surgical bone removal tools, e.g., the Medtronic Straightshot® M4 (or M5) and enables a surgeon to rapidly shave bone or tissue without thermal burn by rotating an inner tube 440 (shown in phantom) relative to a middle tube 430 and drawing debris through an inner lumen 443 defined in the inner tube 440 along a suction path "S" via a suction source 172 (FIG. 1).

More particularly, inner tube 440 is concentrically disposed within the middle tube 430 and includes an opening 445 at a distal end thereof. Distal cutting teeth 441 (shown in phantom) are disposed around the peripheral edge of the opening 445. Inner tube 440 is configured to connect to a power source 162 (FIG. 1) and is selectively activatable to rotate relative to middle tube 430. Middle tube 430 is concentrically disposed within the outer tube 450 and includes an opening 435 defined at a distal end thereof. Distal cutting teeth 4311 are disposed around the peripheral edge of the opening 435 of the middle tube 430. Openings 445 and 435 are disposed in longitudinal registration relative to one another (i.e., in alignment along the longitudinal axis A-A defined through outer tube 450) such that, upon rotation of the inner tube 440 relative to the middle tube 430, tissue or bone disposed in the cutting window defined between the openings 435, 445 is cut or shaved by the cooperating series of teeth 431, 441 at a high speed.

In one embodiment, irrigation fluid "F", e.g., saline, is supplied from a fluid source, e.g., fluid source 152 of FIG. 1, in a channel defined between the inner diameter of middle tube 430 and the outer diameter of inner tube 440 and to respective openings 435 and 445 thereof, such that upon rotation of the inner tube 440 relative to the middle tube 430, the cooperating teeth 431, 441 shave bone or tissue disposed within the openings 435, 445 while suction from the suction source, e.g., suction source 172 of FIG. 1, draws debris through the inner lumen 443 along the suction path "S".

As mentioned above, one of the advantages when using the prior art surgical hone removal tools, e.g., the Medtronic Straightshot® M4 (or M5) (hereinafter microdebrider 700 of FIG. 8) is the ability to rotate the inner tube relative to the middle tube three-hundred sixty degrees (360°) to excise tissue and bone without rotating the outer tube 450. This gives a surgeon a wide degree of flexibility when using a navigation system (hereinafter system 600) in that any number of blades 400 having varying angles alpha "α" (FIG. 8) can be attached to the microdebrider 700 and tissue or bone can be easily excised.

Figure 8:
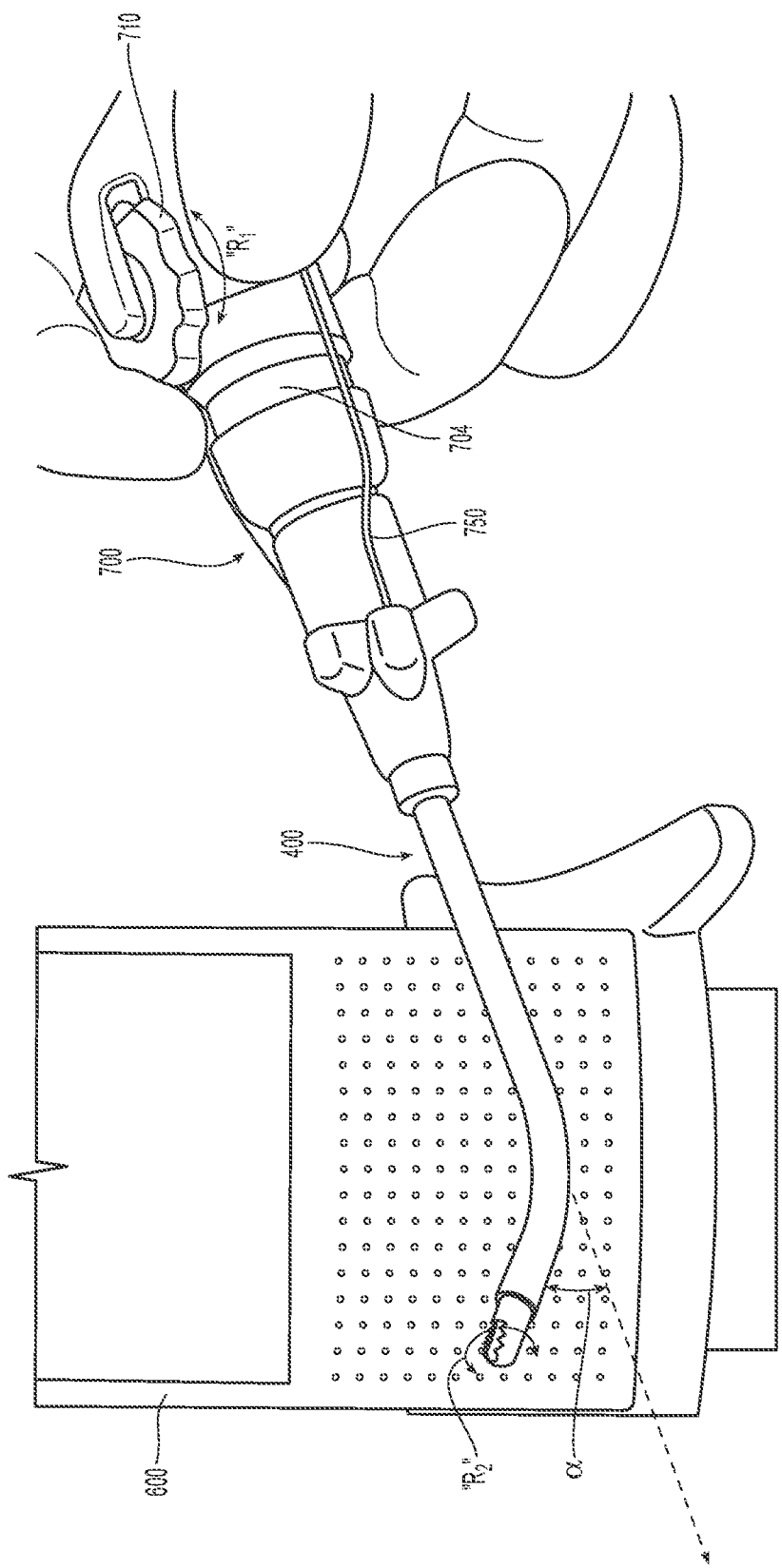
FIG. 8 is a side, perspective view of the blade of FIG. 6 shown assembled on a tissue removal system and being used in conjunction with a surgical navigation system.

More particularly, and with particular reference to FIG. 8, microdebrider 700 may be configured to operably engage blade 400 having inner tube 440, middle tube 430 and outer tube 450 and attach to an irrigation source 750 (FIG. 8) and a suction source 172 (FIG. 1) as described above. A rotation wheel 710 is disposed atop the housing 704 and configured to operably communicate with the inner and middle tubes 440, 430 and is selectively rotatable in direction "$R_1$" to permit 360° of selective rotation in direction "$R_2$" of the cutting window between openings 445, 435 of the inner and middle tubes 440, 430, respectively, without requiring reorientation of the microdebrider 700 in situ. In some embodiments, the rotation wheel 710 may be operably coupled to the middle tube 430.

The combination of the surgeon being able to initially determine the most efficient angle α for the blade 400 at the onset of the surgery (or selectively switch blades 400 as needed during surgery), the ability of the surgeon to rotate the cutting window between the inner and middle tubes 440, 430 with the rotation wheel 710 without reorientation of the blade 400 in situ, and the use of the navigation system 600, all enhance the surgeon's ability to perform the overall surgical procedure.

When using navigation system 600 with prior art blades (not shown) configured to operably connect to the Medtronic Straightshot® M4 (or M5) having an angle α greater than forty degrees (40°), the stability of the middle tube and outer tube was unpredictable affecting the reliability of the navigation system 600. The issue was exacerbated when using prior art blades with greater angles α and at different cutting window rotational positions "$R_1$" due to the forces on the middle tube 430 and outer tube 450 interface associated with cutting tissue or bone in one rotational position, e.g., "$R_1$", versus at different rotational positions, e.g., "$R_2$".

Figure 7:
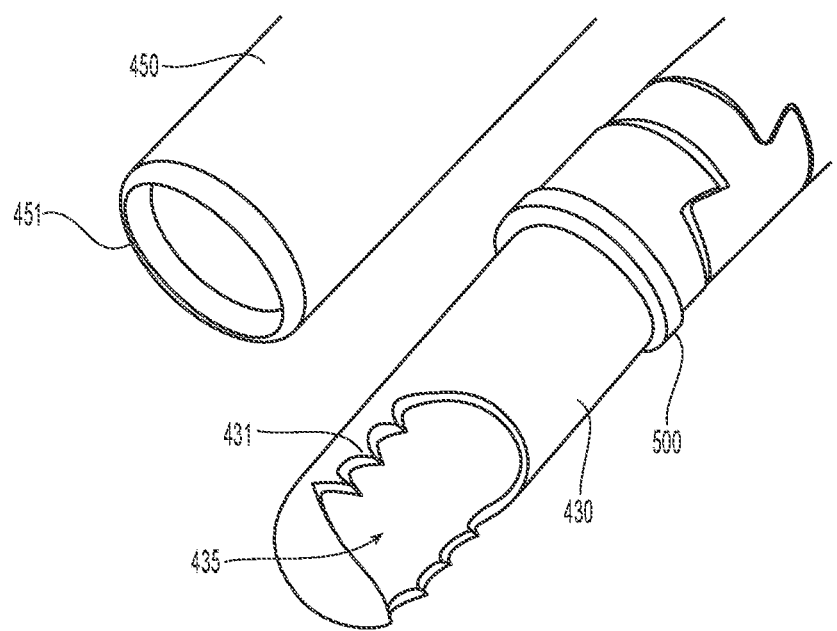
FIG. 7 is an enlarged, perspective view of the blade shown in FIG. 6 with parts separated.

Turning briefly back to FIGS. 6 and 7, which details the presently disclosed blade 400, a distal end of the outer tube 450 is manufactured (e.g., roiled and reamed) to form an inner lip 451 configured to seat a bushing 500 thereagainst when middle tube 430 is inserted within the outer tube 450. Although bushing 500 may take on many forms, in one embodiment, bushing 500 takes the form of a washer and includes an inner diameter that is configured to slide atop an outer surface 430a of middle tube 430 in a tight, friction-fit manner. A shoulder 437 is machined or otherwise formed on the outer surface 430a of the middle tube 430 and is configured to seat a proximal facing surface 502a of the bushing 500 thereagainst. When the middle tube 430 is inserted within the outer tube 450, a distal facing surface 502b of bushing 500 abuts the inner lip 451 while the proximal facing surface 502b is maintained by the shoulder 437 of middle tube 430 thereagainst. As can be appreciated, bushing 500 enhances the interface between the outer tube 450 and the middle tube 430. It is contemplated that bushing 500 enhances the middle tube 430 and outer tube 450 interface such that blades 400 having angles α up to about 90° remain reliable without affecting the stability of navigation system 600. Moreover, the bushing 500 is configured to maintain the stability of the interface between the outer tube 450 and the middle tube 430 when the rotating wheel 710 is rotated to reorient the cutting window between openings 435, 445 to position, e.g., "R₂", wherein the cutting forces associated with thick tissue or bone may be higher than with a different position, e.g., "R₁".

It is contemplated that bushing 500 may be made from any suitable type of material, such as a polymer, and may be of varying thicknesses, lengths and diameters to enhance the stability between tubes 450, 430, blade 400 or microdebrider 700.

While several aspects of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

It will be understood that various modifications may be made to the aspects and features disclosed herein. Therefore, the above description should not be construed as limiting, but merely as exemplifications of various aspects and features. Those skilled in the art will envision other modifications within the scope and spirit of the claims appended hereto.

What is claimed is:

1. A device for removing tissue or bone, comprising:
   a housing having an outer tube extending therefrom including a longitudinal axis defined therealong, the outer tube including a distal end defining an inner lip on an inner periphery thereof;
   a middle tube operably supported concentrically within the outer tube, the middle tube including an opening having a series of teeth at a distal end thereof and a shoulder defined around an outer peripheral surface thereof;
   an inner tube concentrically disposed within the middle tube including an opening having a series of teeth at a distal end thereof in longitudinal registration with the opening in the middle tube, the inner tube adapted to couple to a power source such that, upon activation thereof, the inner tube rotates relative to the middle tube and the series of teeth of the inner tube cooperates with the series of teeth of middle tube to cut tissue or bone disposed in a cutting window between the openings defined therebetween; and
   a bushing disposed on an outer surface of the middle tube in abutting relation against the shoulder, such that, upon assembly, the bushing seats in axial, abutting retention between the shoulder of the middle tube and the inner lip of the outer tube, the seating of the bushing in axial, abutting retention configured to maintain the stability of an interface between the outer tube and the middle tube when the cutting window between the openings is reoriented.

2. The device for removing tissue or bone according to claim 1, wherein the distal end is rolled and reamed to form the inner lip.

3. The device for removing tissue or bone according to claim 1, wherein the inner tube defines a lumen therethrough and extending therealong from the opening, a portion of the lumen adapted to connect to a suction source for eliminating cut tissue or bone.

4. The device for removing tissue or bone according to claim 1, wherein a channel is defined between the concentric inner and middle tubes along a length thereof for passing a fluid therealong from a fluid source.

5. The device for removing tissue or bone according to claim 1, further comprising a rotating wheel disposed atop the housing, the rotating wheel configured to permit selective 360° of rotation of the cutting window defined between respective openings of the middle and inner tubes without repositioning the outer tube.

6. A system for removing tissue or bone, comprising:
   a housing adapted to connect to a power source, a fluid source and a suction source, the housing including an adapter configured to operably connect to a selectively removable blade, the selectively removable blade having a blade angle of about 12° to about 90° and including:
   an outer tube extending therefrom including a longitudinal axis defined therealong, the outer tube including a distal end defining an inner lip on an inner periphery thereof;
   a middle tube operably supported concentrically within the outer tube, the middle tube including an opening having a series of teeth at a distal end thereof and a shoulder defined around an outer peripheral surface thereof;
   an inner tube concentrically disposed within the middle tube including an opening having a series of teeth at a distal end thereof in longitudinal registration with the opening in the middle tube, the inner tube adapted to couple to a power source such that, upon activation thereof, the inner tube rotates relative to the middle tube and the series of teeth of the inner tube cooperate with the series of teeth of middle tube to cut tissue or bone disposed in a cutting window defined in the openings defined therebetween; and
   a bushing disposed atop the middle tube in abutting relation against the shoulder, such that, upon assembly, the bushing seats in axial, abutting retention between the shoulder of the middle tube and the inner lip of the outer tube, the seating of the bushing in axial, abutting retention configured to maintain the stability of an interface between the outer tube and the middle tube when the cutting window between the openings is reoriented.

7. The system for removing tissue or bone according to claim 6, wherein the system is adapted to connect to a navigation system.

8. The system for removing tissue or bone according to claim 6, wherein the distal end of the outer tube is rolled and reamed to form the inner lip.

9. The system for removing tissue or bone according to claim 6, wherein the inner tube defines a lumen therethrough and extending therealong from the opening, a portion of the lumen adapted to connect to the suction source for eliminating cut tissue or bone.

10. The system for removing tissue or bone according to claim 6, wherein a channel is defined between the concentric inner and middle tubes along a length thereof for passing a fluid therealong from the fluid source.

11. The system for removing tissue or bone according to claim 6, further comprising a rotating wheel disposed atop the housing, the rotating wheel configured to permit selective 360° of rotation of the cutting window defined between respective openings of the middle and inner tubes without repositioning the outer tube.

\* \* \* \* \*